(12) United States Patent
Strano et al.

(10) Patent No.: US 12,290,415 B2
(45) Date of Patent: May 6, 2025

(54) METHOD FOR DELINEATING AND LINKING/CORRELATING OPPOSING MARGINS OF A PATHOLOGY SPECIMEN AND IMMEDIATELY ADJACENT REMAINING IN VIVO MARGINS

(71) Applicant: SPRINGLOC LTD, Jerusalem (IL)

(72) Inventors: Shalom Strano, Jerusalem (IL); Alexander Lomes, Moshav Hosen (IL); Steve Krupa, Haifa (IL)

(73) Assignee: SPRINGLOC LTD., Jerusalem (IL)

( * ) Notice: Subject to any disclaimer, the term of this patent is extended or adjusted under 35 U.S.C. 154(b) by 341 days.

(21) Appl. No.: 18/091,912

(22) Filed: Dec. 30, 2022

(65) Prior Publication Data
US 2023/0149119 A1 May 18, 2023

Related U.S. Application Data

(63) Continuation-in-part of application No. 18/083,565, filed on Dec. 18, 2022, and a continuation-in-part of
(Continued)

(51) Int. Cl.
*A61B 90/00* (2016.01)
*A61B 5/06* (2006.01)
(Continued)

(52) U.S. Cl.
CPC ............... *A61B 90/39* (2016.02); *A61B 5/06* (2013.01); *A61B 10/0041* (2013.01);
(Continued)

(58) Field of Classification Search
CPC . A61B 90/39; A61B 90/98; A61B 2090/3908; A61B 2090/3954; A61B 2090/3966; A61B 5/06; A61B 10/0041
See application file for complete search history.

(56) References Cited

U.S. PATENT DOCUMENTS 9,713,437 B2 7/2017 Fullerton et al.
10,154,799 B2 12/2018 van der Weide et al.
(Continued)

OTHER PUBLICATIONS

Samuel Jigme Harrison and Zhang Yue Ping, A 60 Ghz Analog Phase Shifter In 65 NM Bulk CMOS Process, Jul. 2010 p. 13-20 International Journal of Computer Networks & Communications (IJCNC), vol. 2, No. 4.
(Continued)

*Primary Examiner* — Chao Sheng
(74) *Attorney, Agent, or Firm* — Smith Tempel Blaha LLC; Gregory Scott Smith

(57) ABSTRACT

The disclosure is directed to a novel technique for anatomically orientating a removed tissue specimen with the margins of the tissue from which it has been removed. An example process of marking the margins of the excised surgical specimen and the anatomically adjacent in vivo margins can be implemented by a surgeon at the time of removal of the surgical specimen. After removing the surgical specimen from its adjacent tissue, a surgical cavity is generated. Thereafter, locations around the surface margins of the specimen and appropriate locations on the margins of the surgical cavity are marked with one or more pairs of markers (SpM and IVM respectively) with matching identities.

23 Claims, 3 Drawing Sheets

Related U.S. Application Data application No. 17/841,663, filed on Jun. 16, 2022, and a continuation-in-part of application No. 17/724,487, filed on Apr. 19, 2022, said application No. 17/841,663 is a continuation-in-part of application No. 17/724,487, filed on Apr. 19, 2022.

(60) Provisional application No. 63/296,465, filed on Jan. 4, 2022, provisional application No. 63/293,643, filed on Dec. 23, 2021, provisional application No. 63/231,243, filed on Aug. 10, 2021, provisional application No. 63/218,973, filed on Jul. 7, 2021, provisional application No. 63/179,893, filed on Apr. 26, 2021.

(51) Int. Cl.
*A61B 10/00* (2006.01)
*A61B 90/98* (2016.01)

(52) U.S. Cl.
CPC ...... *A61B 90/98* (2016.02); *A61B 2090/3908* (2016.02); *A61B 2090/3954* (2016.02); *A61B 2090/3966* (2016.02)

(56) References Cited

U.S. PATENT DOCUMENTS

| | | |
|---|---|---|
| 10,827,949 B2 | 11/2020 | Greene et al. |
| 10,849,529 B2 | 12/2020 | Brander et al. |
| 2019/0365279 A1* | 12/2019 | Fullerton ............ A61B 5/6847 |

OTHER PUBLICATIONS

FCC Online Table of Frequency Allocations, 47 C.F.R. § 2.106, Revised on Feb. 1, 2021.

Suren Stolik, Anasagasti Lorenzo, Measurement of the penetration depths of red and near infrared light in human "ex vivo" tissues, Journal of Photochemistry and Photobiology B Biology • Oct. 2000 p. 90-93.

Rongge Yan, Xiaoting Guo, Shaoqing Cao, and Changgeng Zhang, Optimization of output power and transmission efficiency of magnetically coupled resonance wireless power transfer system, Published by the American Institute of Physics, View online: https://doi.org/10.1063/1.5007276.

NTAG203 NFC Forum Type 2 Tag compliant IC with 144 bytes user memory, Rev. 3.0—Oct. 17, 2011 213830 Product data sheet, 9. https://cdn-shop.adafruit.com/productfiles/4034/P4034_datasheet_NTAG_203.pdf.

Hologic Inc ("LOCalizer"): https://hologicbreastsurgery.com/en/portfolio/localizer-wire-free-guidance-system/.

* cited by examiner

METHOD FOR DELINEATING AND LINKING/CORRELATING OPPOSING MARGINS OF A PATHOLOGY SPECIMEN AND IMMEDIATELY ADJACENT REMAINING IN VIVO MARGINS

CROSS-REFERENCE TO RELATED APPLICATIONS

This utility patent application is being filed in the United States as a non-provisional application for patent, claiming the benefit of the prior filing date under Title 35, U.S.C. § 119(e) of the U.S. provisional application for patent that was filed on Jan. 4, 2022 and assigned the Ser. No. 63/296,465, and this utility patent application is also a continuation-in-part of United States non-provisional application for patent that was filed on Apr. 19, 2022 and assigned the Ser. No. 17/724,487, and this utility patent application is also a continuation-in-part of United States non-provisional application for patent that was filed on Jun. 16, 2022 and assigned the Ser. No. 17/841,663, and this utility application is also a continuation-in-part of United States non-provisional application for patent that was filed on Dec. 18, 2022 and assigned Ser. No 18/083,565. Each of the above-identified patent applications and the applications they incorporate by reference are all incorporated by reference herein in their entirety.

FIELD OF THE DISCLOSURE

The present disclosure relates to the field of associating margins of excised tissue specimens with their anatomically adjacent in vivo margins in order to facilitate further pathological, diagnostic, surgical or therapeutic procedures.

BACKGROUND

After the clinical detection of a palpable body-of-tissue (BOT) or after the detection of a non-palpable BOT, by mammography, ultrasound, Magnetic-Resonance-Imaging (MRI), Computed-Tomography (CT) or other imaging systems, or at endoscopy or similar procedures; there can be a need to excise this BOT. In such instances, the nature of the BOT may be known (being malignant, benign or indeterminate in nature) or unknown. In cases where the BOT requires full excision, the aim is to remove the BOT in its entirety together with clear surgical margins and to anatomically orientate and designate the specimen excised so that in the event of the pathology margins not being clear, they can be correlated accurately with the corresponding surgical bed margins. The surgeon can then return and remove further specific tissue to establish clear surgical margins.

Current surgical practice is to dissect and remove the tissue specimen from the body, with or without shavings from the walls of the surgical cavity, and to approximately orientate its anatomical relationship to the remaining surgical bed/cavity and its margins by use of a grid system, sutures, metallic clips or the like. The removed specimens' surfaces are then stained with differing-colored inks and dyes.

The excised BOT can be marked by attaching different numbers of inert elements like clips or sutures of differing number and lengths at various orientations on the specimens' margins so as to indicate the superior, inferior, medial, lateral, posterior and anterior margins, for example. The superior margin can be marked with one clip, the inferior margin with two clips, the medial margin with three clips and the lateral margin with four clips, etc. These elements are not uniquely identifiable one from the other, for example. The current method of processing and demarcating the pathology specimen is universally practiced, has been unchanged for several decades and is imprecise and problematic.

The in vivo surgical bed or cavity which previously juxtaopposed the now removed specimen is currently randomly marked with elements such as static inert surgical clips to merely indicate the site of surgery but with no definitive accurate indication of the original anatomical orientation of the surgical margins, being the superior, inferior, medial, lateral, posterior or anterior margins, relative the removed tissue specimens' margins. These elements are currently not uniquely identifiable one from the other.

After removing the BOT and closing the surgical bed, the surgical bed changes its shape, form and size. Consequently, the surgical pathology specimen and the surgical bed or cavity, are only approximately orientated by currently used markings. This problem is emphasized in cases incorporating oncoplastic procedures where large volumes of tissue including the remaining in vivo surgical margins are mobilized over large distances in order to achieve cosmetically acceptable results. The result is that there is a lack of accurate matching of the previously opposing margins.

Therefore, in the event of the pathological assessment of the body of removed tissue it is established that the surgical margins are not clear and that there is a need to return to the surgical site and remove further tissue so as to establish clear surgical margins, the orientation established with elements such as but not limited to surgical clips or sutures or similar devices only somewhat assist the surgeon in estimating which tissue needs further excision in order to establish pathologically clear surgical margins.

In some instances, shavings of further tissue are taken from the remaining walls of the surgical bed or cavity, their approximate anatomical position being recorded by the surgeon and conveyed to the pathologist.

The surgeon currently may also convey the orientation of the excised material by the use of a board or similar surface with a grid system, recording by use of a diagram the approximate position of the specimen and shavings relative to the surgical bed and or cavity.

The long-established imprecise methods described above have been employed by surgeons and pathologists over an extended period of several decades. Accordingly, there is a need for more precise apparatus and methods for marking and accurate matching of the margins of the excised surgical specimen and their anatomically adjacent in vivo margins in order to facilitate further pathological, diagnostic, surgical or therapeutic procedures.

Along the disclosure and the claims, the terms, surgical specimen, surgical pathology specimen, tissue, tissue specimen, excised tissue, surgical bed, surgical cavity, in vivo surgical margin, site or cavity can be used interchangeably. The terms intraoperatively, intra procedurally, at time of biopsy, etc. represent the event of removing a BOT and are used interchangeably. The terms removal, surgery, time of surgery, surgical removal, biopsy etc. represent the surgery, open surgery, endoscopic or video assisted procedures and the like, and can be used interchangeably. The term surgeon can be understood to represent any professional performing the biopsy, an endoscopist, for example etc. The terms hand-held locator, hand-held reader, hand-held device, locating device, and hand-held reader device can be used interchangeably.

BRIEF SUMMARY

The needs and the deficiencies that are described above are not intended to limit the scope of the inventive concepts of the present disclosure in any manner. The needs are presented for illustration only. The disclosure is directed to a novel technique for associating a removed tissue specimen with the margins of the tissue from which it has been removed.

An example process of marking the margins of the excised surgical specimen and the anatomically adjacent in vivo margins that can be implemented by the surgeon at the time of removal of the surgical specimen is disclosed.

The surgeon dissects the specimen to be removed and frees it from adjacent tissue. Whilst the specimen is free and orientated with its adjacent in vivo surgical cavity margins, the margins of the specimen and the surgical cavity are marked with one or more pairs of markers. Each pair of markers constitutes a set. Along the disclosure and the claims the terms 'set of markers' and 'pair of markers' may be used interchangeably.

The markers of each set share an identity (ID) which is unique and different from the identity of other sets of paired markers. Each set serves to designate a specific anatomical location on the opposing margins of the pathology specimen and the immediately adjacent remaining in vivo surgical margin. This is achieved by attaching one marker of the set on the excised/biopsied pathology specimen surface and the other marker of the set on the immediately adjacent opposing in vivo remaining tissue surface. Since the pair of markers of the set shares an ID, the two opposing surfaces are now matched in their orientation to each other. The markers comprising the set may also be referred to as 'sister' markers. Multiple sets constitute a team of markers.

In the event of positive pathological margins and the need to return to the surgical site and accurately remove further tissue to establish clear surgical margins, the exact relevant in vivo sister markers delineating the area of the residual suspicious pathology constituting the positive surgical margin, can be identified and located with a locator devise, for example. The relevant marker/s designating the in vivo anatomical site of residual tissue requiring further surgical removal can also be detected by the surgeon by using a marker/locator system as described in U.S. Ser. No. 17/841,663.

The surgeon may use/attach one or more sets of markers. Each set may comprise an in-vivo marker (IVM) and a specimen-marker (SpM). The specimen-marker (SpM) can be attached to an excised/biopsied pathology specimen surface and the in-vivo-marker (IVM) can be attached to the adjacent opposing in vivo remaining tissue surface. The markers constituting the set can be associated with unique identifiable features, ID features. An example of an ID feature can be a unique electronic ID. In some embodiments the associated ID feature can be a unique visible ID (VID). The unique VID can be established by at least one feature from a group of features. Some examples of VID features can include; radio opaque markings, antennae shape, the shape of an attached external-identification-element (EIE), unique ridges on the markers surface, unique interspaced gaps in the markers metallic coil winding and attached rings and clips, for example. A reader who wishes to learn more about these features is invited to read US2022/0338953. Some embodiments may use the unique electronic ID together with the unique VID's.

More than one set of markers can be used. In such cases, the markers can be placed on a three-dimensional BOT for example as follows. SpMs can be attached to the superior, inferior, medial, lateral, anterior and posterior margins of a pathology specimen with sister markers of each set, ie IVMs, attached to the corresponding in vivo margins. In such an example, the pathology specimen BOT is now defined by six markers which in turn define eight triangles on the surface of the pathology specimen. Each triangle is defined by three SpMs, each marker with its own unique ID. Each triangle can be stained with a different colored ink/dye. When processing the specimen and assessing the pathology margins, a positive margin will be defined by the three SpMs, which constitute that triangle of uniquely stained tissue surface. The positive in vivo surgical margin will consequently be defined by the corresponding three sister IVMs. By localizing these three IVMs, the area of tissue containing the residual unexcised tumor can be removed.

The markers of the set may also be joined. In the case of joined markers, at least two markers can be attached at their ends by a spring, for example (see US 2022/0338953). The set may consist of two single independent markers or one single and two joined markers or two, joined markers. The team of markers may be packaged to comprise a kit of markers.

In an example process of the disclosed technique, each marker of a set can be associated to the specimen or in vivo tissue for example by stitching the marker to the tissue. In another example of the disclosed technique, a marker can be associated with the relevant tissue by bonding, clipping or implanting it to/into the tissue. After associating the one or more sets of markers, the surgeon may remove the surgical specimen.

In the case of an endoscopy/laparoscopy surgery/biopsy or surgical procedure, the in vivo tissue can be marked with an IVM at the time of the procedure and the removed specimen can be marked with a SpM after its removal.

Each IVM can be associated with a unique electronic ID. The ID can be identified by the use of an interrogating signal such as but not limited to a RFID code signal or electromagnetic signal. The markers can be activated by a signal or respond to a signal. The specific structure of each marker and its components determine its response to the activating or interrogating signal. The markers can be located by a hand-held or robotic or scope mounted, etc reader locator that can identify its unique identity and position in space as disclosed in U.S. Ser. No. 17/841,663. An IVM can have a unique audio sound ID, elicited by an interrogating signal whereby the audio ID is unique to each IVM.

In addition, each IVM can be associated with a unique VID. The VID's can be identified visually by an imaging system such as but not limited to X-Ray, Mammography, CT for example. Examples of IVMs and SpMs are disclosed in U.S. Ser. No. 17/724,487. An example of a system for providing accurate marker localization during surgical procedures is disclosed in U.S. Ser. No. 17/841,663. A reader who wishes to learn more about examples of markers and associating systems is invited to read those patent applications.

The ID of the IVM can also be constituted by markers with both a unique electronic and unique VID. Each SpM can be associated with a unique electronic ID and or a unique VID's. The unique ID of the SpM can represent the same ID as the ID of the IVM of its set. In alternate example embodiments of the disclosed technique, the SpM and the IVM may have different IDs. In such embodiment, the surgeon may manage a program/table in which the surgeon, after associating a pair of SpM and IVM, may record that at a certain point on the surface of the surgical specimen, marker SpM having IDx is associating with marker IVM having IDz. In such an embodiment, the correlation between the SpM and the IVM is done by the surgeon. In this way, markers imaged by X-ray having visible unique identifiable features can be paired with and linked to markers having unique electronic identities.

By attaching one or more pairs of markers, ie, SpM/s to the removed surgical specimen and prior to the closure of the surgical cavity, IVM/s to the margins of its immediately adjacent surgical bed or cavity walls, the opposing margins become linked.

The SpMs (each with an unique electronic ID) attached to the surface of the surgical pathological specimen or specimens can be scanned with a hand-held locator prior to pathological sectioning. Each marker point on the surface margin of the specimen is thus uniquely identified and recorded. This enables for a more accurate designation, orientation and color staining of the excised specimen's surfaces and margins than is currently universally practiced. A detailed designation of the pathology specimen surface margins is also achievable with SpM's with unique VID's or SpM's with combined electronic and VID's.

The surface margins can also be designated with a standard clock face pattern with positions on the specimen and the surgical cavity designated as numbers of the clock face, for example. More than one marker set may be used to designate a margin or clock face position and any individual plan and method of marking and orientation is possible and workable.

In the event of positive pathological margins and the need to accurately remove further tissue to establish clear surgical margins, the IVM/s corresponding to the SpM/s of the positive pathology margins can be identified and located. This localization can be done with a locator applied externally and or intraoperatively at the time of repeat surgery. They can also be uniquely identified and localized by their unique visible ID for example at Xray such as Mammography. An example of a locator system is disclosed in US application for patent Ser. No. 17/841,663.

In this manner, the surgeon is enabled to accurately return and zone in on the IVM/s associated with the remaining involved part of the surgical site and remove further tissue and thereby attain clear pathology/surgical margins.

A part from indicating the specific site for further surgery, the IVM in the surgical bed may physically mark the position for further surveillance and or the place for therapy such as irradiation by an electron or proton accelerator or with other relevant modality or modalities.

As the markers may move within the body, it is important that a marker can be associated with one or more fixing elements that prevent its migration. A marker set comprising the SpM and the IVM can be fixed to a BOT, being removed biopsied tissue and or shavings and the immediately adjacent anatomically orientated tissue/surgical surface, with sutures, clips, or other fixation technique thereby ensuring their permanent positions.

An example of a fixing element of the IVM and SpM's can be a ring that is attached to each marker. This ring can be used for stitching the markers to the tissue. Example embodiments of IVM and SpM sets that use joined markers may use a spring that connects the markers as a fixing element for a stitch for example.

Further, the SpM and the IVM can be observed by appropriate modalities such as X-ray, mammography, ultrasound, CT or MRI. The IVM can be constituted without a ferrous content and imaged at MRI without significant artifact.

In the event of there being positive margins, the surgeon can be guided to the specific in vivo markers associated with the area of residual tumor by the use of an Augmented Reality system. These relevant IVM's can be identified by an Augmented Reality system as disclosed in U.S. 63/293,643, which is incorporate herein as appendix A.

Some examples of the novel marker may comprise a uniquely identifiable component of the marker that can be seen with an ultrasound system. Such an example marker can be coated with a hydrophilic material such as but not limited to hydro gel material, for example.

Additional information related to the patient or the procedure or each unique marker may be attached to or encoded on or within the markers, digitally or in other forms.

The markers can be placed in a kit so that the sets of markers with their unique ID's are clearly identifiable in that for example they are color or sequentially number designated, visible to the eye and free to be handled manually and with instruments and clipped, sutured or attached etc. to the surface of the relevant tissue being the biopsy specimen, surgical specimen, margin shavings and the remaining in vivo tissue/cavity walls. The team of markers can be arranged in the kit so that each set is placed in an orientation and labelled so as to simulate the anatomical position of their prospective placement being for example superior, inferior, medial lateral, anterior, posterior or for example but not limited to 12 o'clock, 3 o'clock, 6 o'clock, 9 o'clock positions, and where the markers in the sets are designated as having the same ID by a similar like color or other identifying characteristic visible to the eye. Markers for endoscopic etc placement can also have a relevant arrangement whereby the markers off each set are uniquely identified for placement.

The foregoing summary is not intended to summarize each potential embodiment or every aspect of the present invention, and other features and advantages of the present invention will become apparent upon reading the following detailed description of the embodiments with the accompanying drawings and appended claims.

Furthermore, although specific examples of embodiments are described in detail to illustrate the inventive concepts to a person skilled in the art, such embodiments can be modified to various modifications and alternative forms. Accordingly, the figures and written description are not intended to limit the scope of the inventive concepts in any manner.

Other objects, features, and advantages of the present invention will become apparent upon reading the following detailed description of the embodiments with the accompanying drawings and appended claims.

BRIEF DESCRIPTION OF THE DRAWINGS

Exemplary embodiments of the present disclosure will be understood and appreciated more fully from the following detailed description, taken in conjunction with the drawings in which.

DETAILED DESCRIPTION

Figure 1:
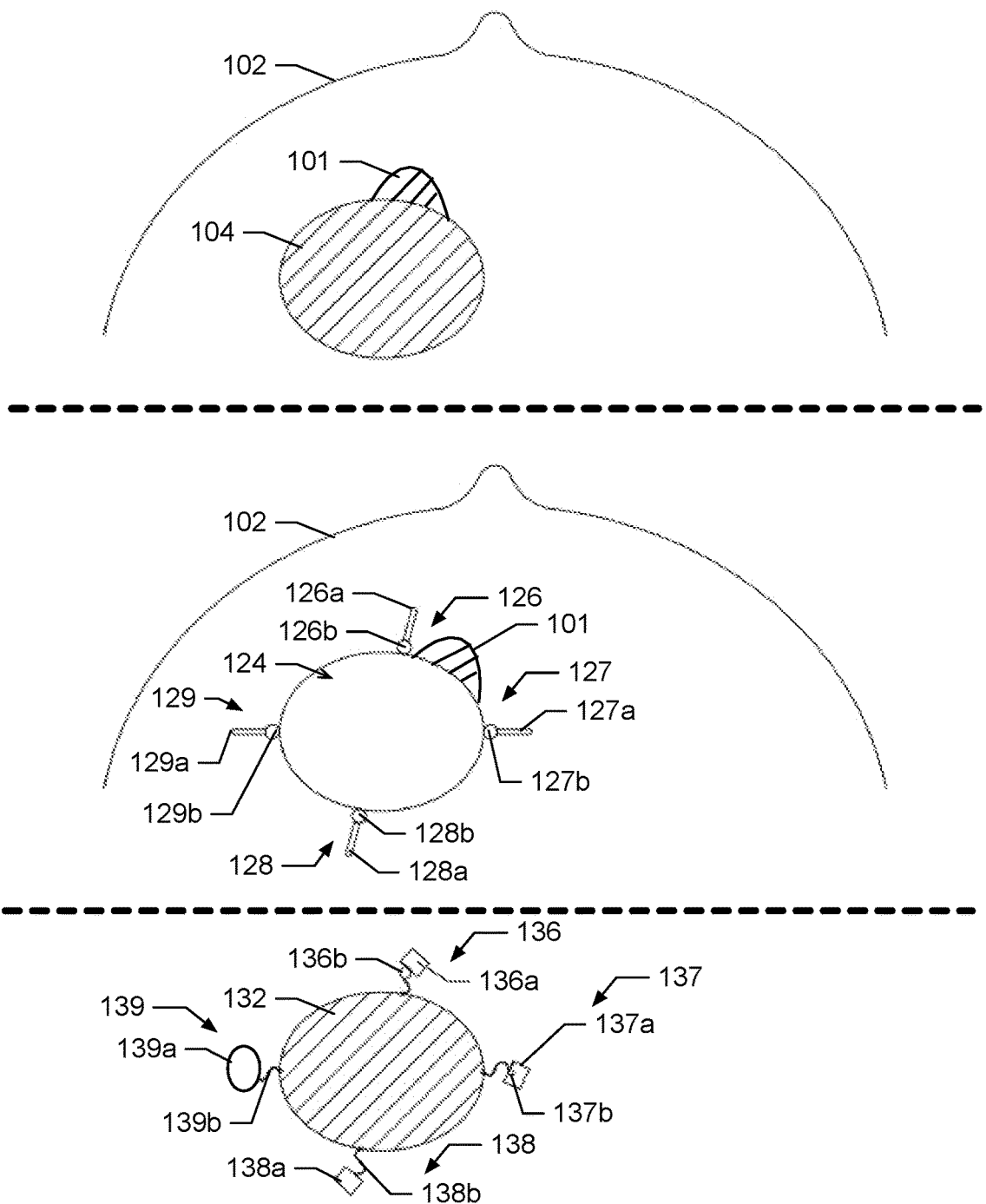
FIG. 1 illustrates steps of removing a BOT from the breast for pathological review with the surgical cavity and the BOT marked with SpM's and IVM's with unique matching electronic ID's.

The invention can be implemented in numerous ways, including a process; an apparatus; a system; a computer program product embodied on a computer readable non-transitory storage medium; and/or a processor, such as a processor is configured to execute instructions stored on and/or provided by a non-transitory memory device coupled to the processor. In this specification, these implementations, or any other form that the invention may take, may be referred to as techniques. In general, the order of the steps of disclosed processes may be altered within the scope of the invention. Unless stated otherwise, a component such as a processor or a non-transitory memory device described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims, and the invention encompasses numerous alternatives, modifications, and equivalents. Numerous specific details are set forth in the following description in order to provide a thorough understanding of the invention. These details are provided for the purpose of example, and the invention may be practiced according to the claims without some or all of these specific details. For the purpose of clarity, technical material that is known in the technical fields related to the invention has not been described in detail so that the invention is not unnecessarily obscured.

Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

In the following description, the words "unit," "element," "module" and "logical module" may be used interchangeably. Anything designated as a unit or module may be a stand-alone unit or a specialized or integrated module. A unit or a module may be modular or have modular aspects allowing it to be easily removed and replaced with another similar unit or module. Each unit or module may be any one of, or any combination of software, hardware, and/or firmware, ultimately resulting in one or more processors programmed to execute the functionality ascribed to the unit or module. Additionally, multiple modules of the same or different types may be implemented by a single processor. Software of a logical module may be embodied on a computer readable non-transitory storage device such as a read/write hard disc, CDROM, Flash memory, ROM, or other memory or storage devices, etc. In order to execute a certain task a software program may be loaded to an appropriate processor as needed. In the present disclosure the terms task, method, process can be used interchangeably. In the present disclosure the verbs transmit, transfer or be placed in a queue can be used interchangeably. Packets that are placed in a queue are sent as soon as possible.

Passive multimodality markers with unique ID's, which respond to an interrogating signal, can be placed in the body and located with a locator. These markers can be attached to the surface/margins of an excised BOT, ie, a pathology specimen, and its directly adjacent remaining in vivo tissue margin surface.

By pairing these markers and by matching their ID's, the specimen removed from the body carries with it the exact orientated matching surface/margin information as the adjacent remaining margin tissue left in the body.

The disclosed technique constitutes a system that can assist the pathologist in the assessment of the said pathological specimen and resulting enable the pathologist to convey to the surgeon whether the lesion has been successfully removed with clear pathology margins or not. By using the paired markers, in the event of involved margins, the pathologist can henceforth guide the surgeon to the specific area of remaining tumor for re excision. Both the location and unique ID of the markers is demonstrable.

The method of attaching the markers to tissue on both the pathology specimen and the adjacent in vivo tissue surface can be with a surgical stitch attached or passed through a metal ring or loop attached to the marker, for example. The term attaching is understood to include, stitched, clipped to, glued to, stuck to, anchored to, placement, implanted, introduced etc.

A ring or a loop attached to the marker can be independent to the contents of the marker. The external antenna/EIE's of the marker may be configured as a ring or loop for a surgical suture or configured as a clip, to enable it to be attached to tissue. The markers can be implanted or attached to tissue with an introducer needle, laparoscope, endoscope or similar surgical device including under imaging or robotic guidance. The locating device used for their detection may be for example machine, robotic, endoscopically, video or hand held/guided.

The following illustrations come to show the steps of how these multimodality markers may be used to mark the adjacent margins of an excised BOT and the remaining biopsy cavity and allows accurate orientation and matching of the adjacent tissue margins. The example chosen is the removal of a malignant breast lesion but the process is understood to be applicable to lesions at other anatomical sites.

The illustrations are diagrammatic and two dimensional. The description for clarity is based on these two-dimensional diagrams. However, it is understood that the principles/meaning contained in the description of the two-dimensional drawings are applicable to the clinical three-dimensional setting. Markers placed on a three-dimensional BOT, such as a pathology specimen, can define specific areas on the surface of that BOT, depending on the number of markers used and the site of their placement/attachment on the said BOT.

For example, SpMs can be attached to the superior, inferior, medial, lateral, anterior and posterior margins of the pathology specimen with sister IVMs of each set attached to the corresponding in vivo margins. In such an example, the three-dimensional pathology specimen BOT is now defined by six markers which in turn define eight triangles on the surface of the pathology specimen. Each triangle is defined by three SpMs, each marker having its own unique ID. Each triangle can be stained with differing colored inks/dyes. When processing the specimen and assessing the pathology margins, a positive margin will be defined by the three SpMs which constitute that triangle of uniquely stained tissue surface. The corresponding positive in vivo surgical margin will consequently be defined by the corresponding three sister IVMs. By localizing these three sister IVMs, the area of tissue containing the residual unexcised tumor (corresponding to the triangle of positive pathology margin) can be removed for example surgically.

FIG. 1 illustrates an in vivo malignant BOT 104 within the breast 102 which requires excision. The BOT 104 once removed constitutes the surgical pathology specimen 132. The space previously occupied by the BOT constitutes the surgical cavity 124. After the surgeon has fully dissected the relevant tissue requiring removal and freed it from the surrounding tissues, the margins of both the surgical specimen 132 and its directly adjacent surgical cavity 124 are marked with sets of markers wherein each marker in the set has a similar electronic ID. However, each set of markers has an electronic ID different to the other placed sets.

The marking may be as per current anatomical position designations (denoting the anterior, posterior, medial, lateral, superior and inferior margins) as described or in another unique way, for example as a clock face, but preferably consistently in the sense that both the operating surgeon and the reporting pathologist are familiar with the methodology of the marking designation in that both are in synch as to the implication of each markers position and number.

One or more marker sets can be placed to achieve the relevant matching margin orientation and designation. In FIG. 1 four marker sets have been used to achieve the margin marking. The marker sets in FIG. 1 are made up by markers (126,136); (127, 137); (128, 138); and (129, 139). Each set of markers has a unique electronic ID different to the electronic ID of other sets. The SpMs of each set (136, 137, 138, 139) are shown to be attached to the surface of the surgical specimen 132. The sister IVMs of the sets (126, 127, 128, 129) are placed on the surface of the surgical cavity 124.

The sister SpM and IVM of each set are fixed at exact opposing locations along the opposing margins so as to create a mirror image of each other. The markers can be fixed at a single or plurality of points around the surgical cavity and its immediately adjacent specimen margins. This exact matching of the SpM and IVM creates an exact matching of locations along the two now separated margins. (The surgical site 124 and pathology specimen 132). The number of markers placed is at the discretion of the surgeon and may exceed the current practice of a singular designation of the specimens' anatomical margins being, superior, inferior, medial, lateral and anterior. The surgical bed 124 is closed, manipulated as for example in an oncoplastic procedure or left as a cavity depending on the surgical preference or circumstance.

The removed malignant BOT 104 now constitutes the pathology specimen 132. The specimen may be x-rayed to confirm the presence of localizing marker/s within it and to establish the unique VID elements of the SpM's. The pathology specimen 132 is passed from the surgical facility to the pathology department for processing.

The pathology department being but not restricted to the pathology technician and or physician, with the aid of a locator, scan the surface of the surgical specimens' margins and locate the individual markers. The SpMs can be scanned with a hand-held device which reads each markers unique electronic ID. By scanning each marker and recording its unique ID, the margins of the specimen are broken down into discretely defined sub set margins ie, areas between specific SpMs.

These sub margins defined by unique SpM's, match/correlate with the matching sister IVM left in vivo. The pathology specimen 132 is now processed. This can involve the unique staining of sub margins. The specimen is then processed, sectioned and read. The pathology report will convey whether the surgical margins are clear in that the lesion of concern has been excised with clear surrounding noninvolved tissue or whether one or more margins are involved by the lesion and require re excision. In the event of one or more of the margins or sub margins, as defined by the SpM's, being involved by suspicious or for example malignant tissue 101, the possibility now exists to specifically correlate the SpMs which defined the positive margin with the same electronic ID IVM sister markers left in vivo.

For example, FIG. 1 shows that area 101 of the original tumor 104 has been left behind in vivo at initial surgery, ie the tumor has been transected by the surgeon and not fully excised. The transected margin being between SpM 136 and 137. The report will convey the area of margin involvement as being between SpM 136 and 137 and therefore also indicate the residual carcinoma 101 area in vivo as being between the sister IVM 126 and 127 of the relevant set. In the case of immediate frozen sectioning of the specimen, the above could also apply.

The surgeon by the use of a locating device can return to the surgical site and locate the IVM/s of the same ID as the SpM/s which defined the positive pathology margins and thereby zone in and remove further tissue 101 for pathological review with the intent of achieving clear surgical margins. This process can be repeated with further re excision of tissue until clear surgical margins are attained. In the case of robotic, endoscopic or for example video assisted procedures, a suitable locator will achieve the same goal.

The IVM's in FIG. 1 (126, 127, 128, 129) are for illustration purposes passive markers (without ferrous content) with unique electronic ID's as described in the related patent applications. The example IVM in FIG. 1 can comprise a microelectronic chip, a magnetic antenna, a dipole microwave antenna embedded within a hermetic bio-compatible container of minimal dimensions made of bio-compatible dielectric material, such as but not limited to glass and/or plastic and a unique electronic ID. Each marker is associated with a unique electronic ID code that is stored in a memory of the microelectronic chip. The stored ID code indicates the unique ID of that marker which matches the electronic ID of its sister SpM (136, 137, 138, 139) respectively.

The external part of the dipole microwave antenna is configured as a ring 126b, 127b, 128b, 129b. The design of these markers and their detection system are described in the related patent applications. The ring may be attached to the body 126a, 127a, 128a, and 129a of the marker.

The SpMs (136, 137, 138, and 139) can be RFID discs (136a, 137a, 138a, 139a) attached or fixed to the specimen with a stitch (136b, 137b, 138b, 139b). The disc of each marker may have unique markings, wording, symbols etc as described in the related patent applications. Along the disclosure and the claims, the verbs attach or fix and conjugates thereof can be used interchangeably.

The SpMs (136, 137, 138, 139) can be attached to the pathology specimen 132 by a stitch 138b, 139b or a clip, for example. FIG. 1 illustrates SpMs 136, 137, 138, 139 embodied as a RFID marker card 136a, 137a, 138a, 139a. They contain a microchip with a unique electronic ID, and are attached to the surgical pathology specimen 132 surface edges. The attachment can be done by stitching. The stitch can be passed through a ring 136b or a hole in the disc 137b. They can be located and their unique electronic ID identified for example by the surgeon and pathologist with a hand-held reader device. These markers may have visual identifying features such as various color markings as well as attached radiopaque markings being shapes, letters, words or numbers, which establish each marker's unique visual identity including by x-ray. These visual identifying features can also be on an independent label attached to the card for example with a thread.

Figure 2:
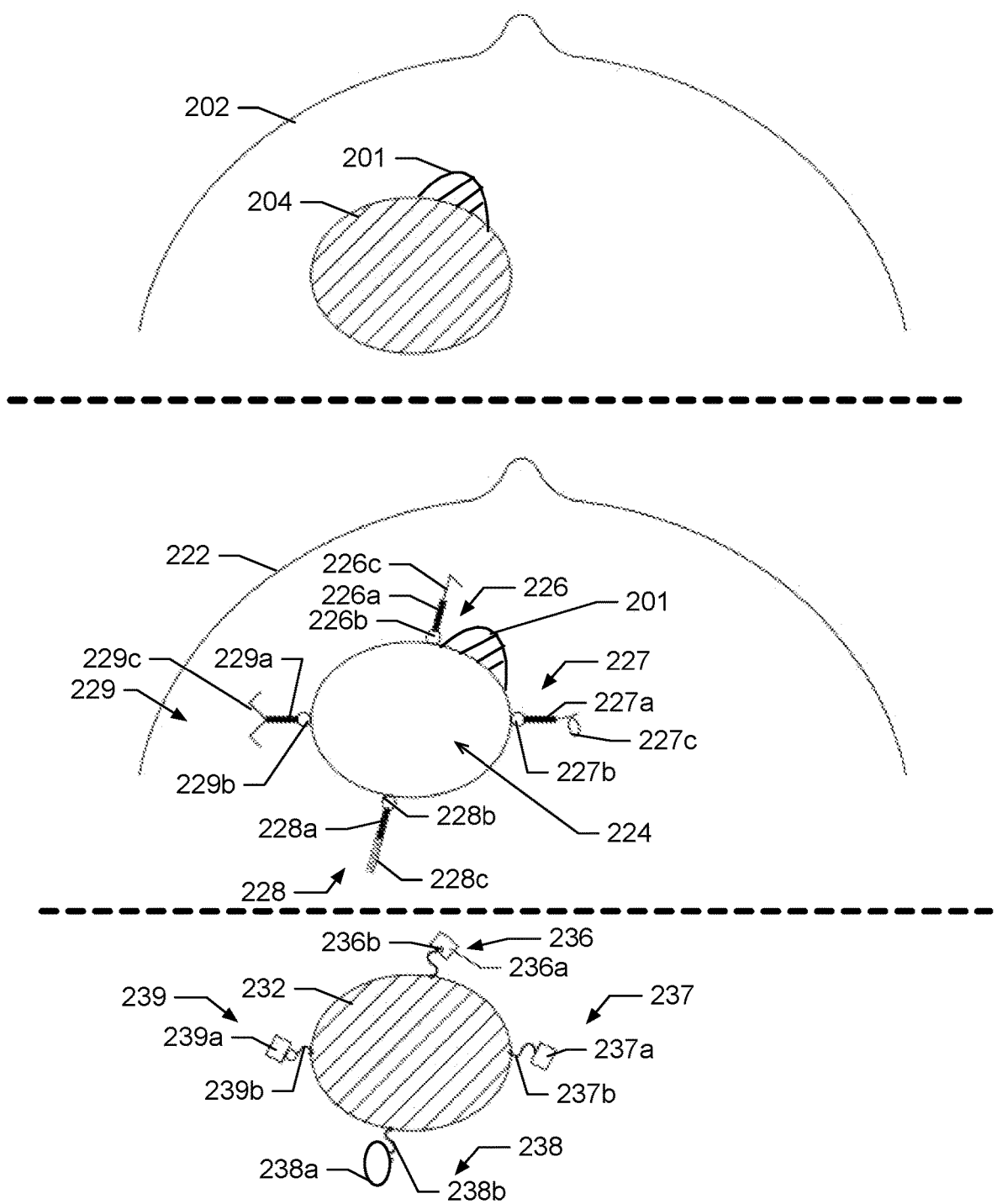
FIG. 2 illustrates steps of removing a BOT from the breast for pathological review with the surgical cavity and pathology margins marked with SpM's and IVM's wherein the IVM's have unique VID's and do not have an electronic ID.

FIG. 2 illustrates the steps of removing a BOT 204 from the breast 202 for pathological review with the surgical cavity 224 marked with IVM's 226, 227, 228, 229 and the pathology surgical specimen 232 marked with SpMs 236, 237, 238 and 239. FIG. 2 illustrates a similar process of tumor removal as described in FIG. 1. However, the IVM's 226, 227, 228 and 229 lack an electronic ID. Instead, each IVM is uniquely identified by a unique VID. The IVM's in FIG. 2 although lacking a unique electronic ID, can also be detected or respond to an interrogating signal. IVM's 226, 227, 228 and 229 may comprise a body of the IVM (226a, 227a, 228a, and 229a respectively), a fixing element (226b, 227b, 228b, and 229b) and an external-identification-element (EIE) (226c, 227c, 228c, and 229c).

Some examples of VID features can include; radio opaque markings, antennae shape, the shape of an attached external-identification-element (EIE) 226c, 227c, 228c and 229c, ridges on the markers surface with unique shapes and or spacing, unique interspaced gaps in the markers radio opaque metallic coil winding and attached rings and clips for example. Some embodiments of the EIE can have a plurality of shapes. The EIE can be built from bio-compatible diamagnetic metal, nitinol or tungsten for example. The EIE can be attached to the marker and act as fixing element that prevents migration. The pathology specimen 232 is marked with SpM's (236, 237, 238 and 239). The SpMs can have a similar structure and unique electronic ID as discussed above with respect to FIG. 1 elements 136, 137, 138 and 139. The unique nature of the EIE's/external antenna of the IVM's and their identification is explained in the related patent applications.

The unique VID's of the IVM's 226, 227, 228 and 229 are established by; a hook 226c attached to the end of IVM body 226a; a loop 227c attached to the end of IVM body 227a; a spring 228c attached to the end of IVM body 228a and double hook 229c attached to the end of IVM body 229a. Rings 226b, 227b, 228b, 229b can be used for stitching/attaching/fixing of IVM's 226, 227, 228 and 229 (respectively) to the margin of the cavity 224. They are attached at the opposite ends of the SpMs 236, 237, 238 and 239 respectively.

The associated matching of the ID of each pair of markers of each set in FIG. 2 is achieved by the surgeon at the time of marker placement, recording the identity of the unique VID and electronic ID of the markers of each set. This record acts as the template for the associated matching of the IVM and SpMs of each set (226&236; 227&237; 228&238; and 229&239).

In the event of positive pathology margins and the need to return and excise further tissue 201, the in vivo IVMs 226 and 227 matched/associated with the SpMs 236 and 237 defining the positive margin 201, can be located by X Ray for example Mammography. These markers can then be discretely localized and allow the surgeon to zero in on the necessary area/s of tissue and thereby attempt to attain clear surgical/pathological margins as described above. In the event of a positive pathology margin 201, the ID of the relevant IVMs (226&227) is conveyed to the surgeon. By matching the unique electronic ID of the relevant SpMs 236 237 designating the position of the residual tumor 201 with the unique IVM's 226, 227 having VID elements 226c, 227c visible on an imaging system for example mammography, the surgeon gains a visual and anatomical orientation which aids in the location of the said markers at repeat surgery. The radiologist also gains information by being able to reassess the imaged tumor bed within the context/vicinity of these relevant markers.

The SpMs 236, 237, 238, 239) are shown as RFID discs/tags (236a, 237a, 238a, 239a) attached to the specimen 232 with a stitch 236b, 237b, 238b, 239b. The disc of each marker may have unique markings, wording, symbols etc as described in the related patent applications.

The SpMs 236, 237, 238, 239 attached to the pathology specimen 232 can be in the form of a water-resistant disc, card or similar configuration 236a, 237a, 238a, 239a with a method of attachment to the pathology specimen such as a stitch or clip, for example. The cards 236a, 237a, 238a, 239a may contain a microchip with a unique electronic ID, and are attached to the surgical pathology specimen 232 margin. The attachment is via a stitch 236b, 237b, 238b, 239b passed through a ring 239b or a hole 236b in the disc. They can be located and their unique electronic ID identified for example by the surgeon and pathologist with a hand-held reader device. These markers may have visual identifying features such as various color markings as well as attached radiopaque markings being shapes, letters, words or numbers, which establish each marker's unique visual identity including by x-ray. These visual identifying features can also be on an independent label attached to the card for example with a thread.

Figure 3:
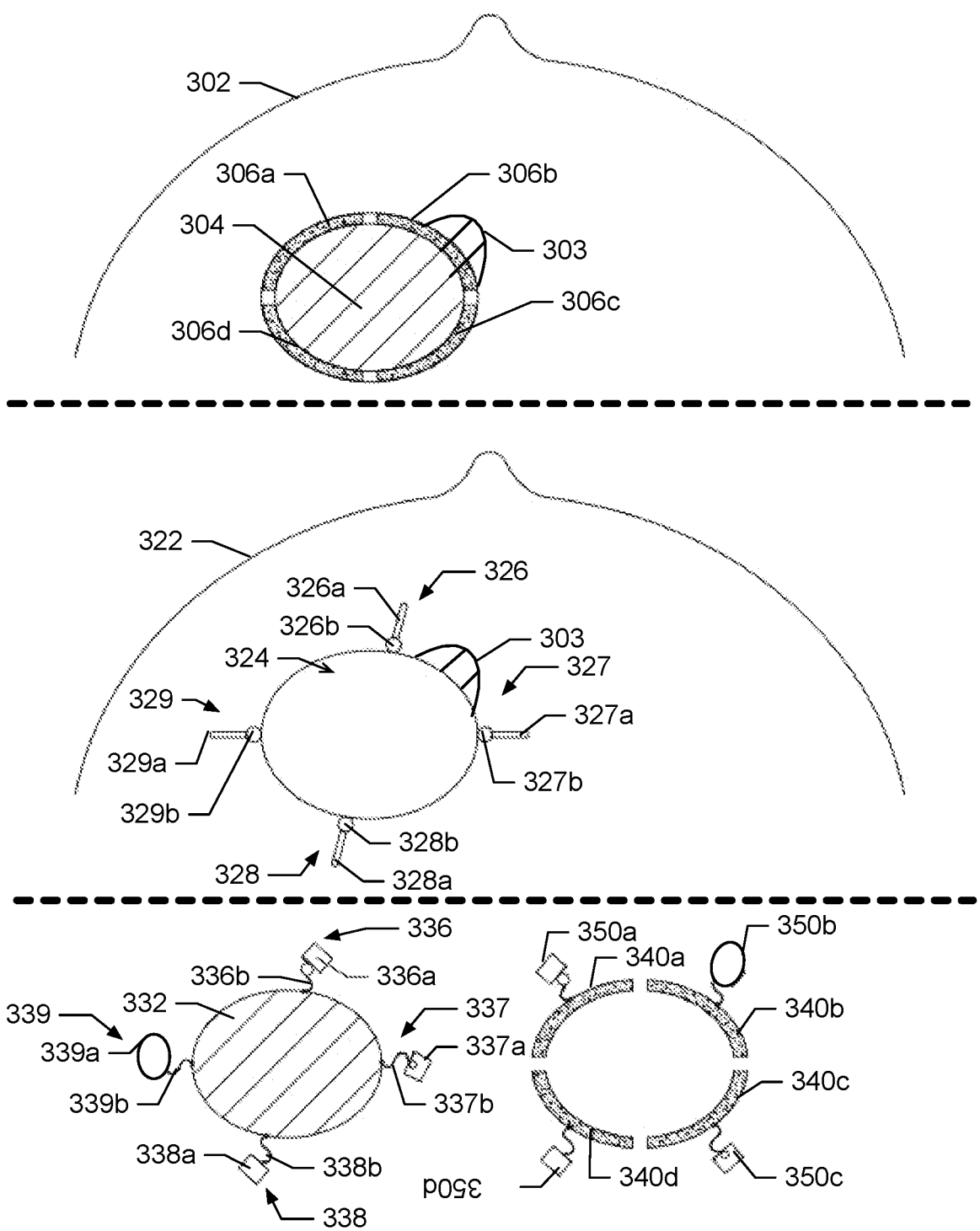
FIG. 3 illustrates steps of removing a BOT from the breast with associated surgical shavings.

FIG. 3 illustrates steps of removing a BOT 304 from the breast 302 with associated surgical shavings 306a, 306b, 306c and 306d. The process is similar to the process that is disclosed in conjunction with FIG. 1. However, after removing the BOT 304 and obtaining the pathology specimen 332, the surgeon thereafter removes further slivers of independent tissue around the margins of the initial surgical cavity 324, referred to as pathology shavings, 340a, 340b, 340c, and 340d. The marking of the final surgical cavity margins 324, ie, the margin created after removal of the BOT 332 and the shavings 340a, 340b, 340c, 340d, is achieved with IVMs 326, 327, 328, 329. The IVMs 326, 327, 328, 329 can be similar to the IVM's 126, 127, 128, 129 in FIG. 1 with each IVM 326, 327, 328, 329 having a unique electronic ID. Each IVM consists of a body 326a, 327a, 328a, 329a and an attached ring 326b, 327b, 328b, 329b. The ring can be used to assist fixation of the associated IVM to the margin of the cavity 324.

The margins of the pathology specimen 332 and the pathology shavings 340a, 340b, 340c, 340d are marked with SpMs 336,337,338,339 and 350a, 350b, 350c, 350d respectively whereby these markers define the margins and sub margins (pathology shavings) of the pathology specimen 332 and the shavings 340a, 340b, 340c, 340d. The shavings can be fragile and placed in containers. In such instances, SpM's 350a, 350b, 350c, 350d can be attached to/associated with the container/s thereby defining the shavings anatomical orientation and matching them with the sister in vivo IVM's 326, 327, 328, 329. A separate card/tag can also be attached to the specimen bottle containing the relevant biopsied shaving specimen/s.

The SpMs 336, 337, 338, 339 are shown as RFID discs/tags 336a, 337a, 338a, 339a attached to the specimen 332 with a stitch 336b, 337b, 338b, 339b. The disc of each marker may have unique markings, wording, symbols etc as described in related patent applications.

The SpMs 350a, 350b, 350c, 350d, which are attached to the shavings, are shown as RFID discs/tags attached to the pathology shaving specimens 340a, 340b, 340c, 340d with a stitch. The disc 350a, 350b, 350c, 350d of each marker may have unique markings, wording, symbols etc. as described in the related patent applications.

The SpM markers 336a, 337a, 338a, 339a that are attached to the pathology specimen 332 can be in the form of a water-resistant disc, card or similar configuration, with a method of attachment to the pathology specimen such as for example with a stitch or clip. SpMs 336, 337, 338, 339 can be embodied as a RFID marker card 336a, 337a, 338a 339a. They can contain a microchip with a unique electronic ID, and are attached to the surgical pathology specimen 332 surface margin. The attachment is via a stitch 336b, 337b, 338b, 339b passed through a ring or a hole in the disc. The stitch can also be attached directly to the disc or a tag.

SpM's 336, 337, 338, 339, 350a, 350b, 350c, 350d can be located on the pathology specimen and the shavings by the surgeon and pathologist with a hand-held reader device that identifies their unique electronic ID, for example. In other embodiments, markers, 336, 337, 338, 339, 350a, 350b, 350c, 350d may have visual identifying features such as various color markings as well as attached radiopaque markings being shapes, letters, words or numbers, which establish each marker's unique visual identity including by x-ray, for example. These visual identifying features can also be on an independent label attached to the card with a thread, for example. The above features can also apply to the marker discs/tags attached to the pathology shavings.

In the event of one or more of the surface margins or sub margins of the pathology specimen and or shavings defined by the SpMs being involved by suspicious or for example malignant tissue, the possibility now exists to specifically correlate the SpM's which defined the positive margin/s with the same electronic ID sister IVMs left in vivo.

Area 303 of the original tumor 304 has been left behind in vivo at initial surgery, ie the tumor has been transected by the surgeon and not fully excised. The transected margin being between SpM's 336 and 337 of the pathology specimen and associated with pathology shaving 340b as defined by SpM 350b. The pathology report will convey this area of margin involvement and therefore also indicate the residual carcinoma 303 area in vivo as being between the sister IVM's 326 and 327 of the relevant sets. The disclosed procedure can be adapted to cases of immediate frozen sectioning of the specimen.

Upon determining that there is residual carcinoma 303, the surgeon by the use of a locating device can return to the surgical site and locate the relevant IVM's 326 and 327 and remove further tissue for pathological review with the intent of achieving clear surgical margins. This process can be repeated with further re excision of tissue until clear surgical margins are attained. In the case of robotic, endoscopic or for example video assisted procedures, a suitable locator will achieve the same goal.

A person having ordinary skill in the art can understand that the disclosed technique can be used for the removal of a BOT from a patient, from the breast for example, where the surgical margins and pathology margins are marked and matched with IVMs and SpMs where some of the markers have unique electronic ID's and some have unique VID's and no electronic ID and some have both a unique electronic ID and a unique VID.

In cases in which the SpMs may have IDs that differ from the ID of the IVMs, the surgeon may manage a program or a table in which the surgeon, after associating the SpMs with the relevant IVM's may record this association. For example, it can be recorded in a computer program or in a table that a certain IVM having IDx is oriented with the removed BOT at a position marked with a SpM having IDy and a shaving if relevant that is marked 'shaving SpM' having IDz. In such embodiment of the disclosed technique, the correlation between the markers associated with the removed BOT, the pathology specimen, the shavings and the markers associated with the walls of the in-vivo cavity, is done by the surgeon.

In the description and claims of the present disclosure, each of the verbs, "comprise", "include", "have", and conjugates thereof, are used to indicate that the object or objects of the verb are not necessarily a complete listing of members, components, elements, or parts of the subject or subjects of the verb. The present disclosure has been described using detailed descriptions of embodiments thereof that are provided by way of example and are not intended to limit the scope of the invention.

The described example embodiments comprise different features, not all of which are required in all embodiments of the invention. Some embodiments of the present invention utilize only some of the features or possible combinations of the features. Many other ramification and variations are possible within the teaching of the embodiments comprising different combinations of features noted in the described embodiments.

It will be appreciated by persons skilled in the art that the present invention is not limited by what has been particularly shown and described herein above. Rather the scope of the invention is defined by the claims that follow.

We claim:

1. A method for removing a body-of-tissue (BOT) from a patient, the method comprising:
   i. excising the BOT thereby generating a cavity;
   ii. fixing one or more in-vivo-markers (IVMs) to walls of the cavity;
   iii. fixing one or more specimen markers (SpMs) to the BOT such that at least one location on the BOT that is associated with an SpM from the one or more SpMs is adjacent to a location in the cavity to which an IVM from the one or more IVMs was fixed thereby generating at least one set of IVM and SpM; and
   iv. wherein at least one IVM from the one or more IVMs is associated with a unique identification (ID) that is configured to be visualized by an imaging system.

2. The method of claim 1, wherein the action of fixing an IVM from the one or more IVMs to the walls of the cavity is implemented by stitching the IVM to the walls of the cavity.

3. The method of claim 1, wherein the action of fixing an IVM from the one or more IVMs to the walls of the cavity is implemented by using clips.

4. The method of claim 1, wherein the action of fixing a SpM from the one or more SpMs to the BOT is implemented by stitching the SpM to the BOT.

5. The method of claim 1, wherein the action of fixing a SpM from the one or more SPMs to the BOT is implemented by using clips.

6. The method of claim 1, wherein the unique ID that is configured to be visualized by the imaging system (VID) is an external-identification-element (EIE).

7. The method of claim 1, wherein the unique ID that is configured to be visualized by the imaging system (VID) are unique ridges on the markers surface.

8. The method of claim 1, wherein the unique ID that is configured to be visualized by the imaging system is unique marker antenna shapes.

9. The method of claim 1, wherein the imaging system comprises a mammography system.

10. The method of claim 1, further comprising recording the one or more sets of IVM and SpM.

11. The method of claim 1, further comprising shaving one or more segments from the walls of the cavity and associating an SpM to at least one segment from the one or more segments.

12. The method of claim 1, wherein a unique electronic ID code, which indicates the unique ID, is stored in a microelectronic chip that is associated with the at least one IVM from the one or more IVMs.

13. The method of claim 2, wherein the microelectronic chip is embedded within a hermetic bio-compatible container.

14. The method of claim 1, wherein an IVM from the one or more IVMs comprises a fixing element.

15. The method of claim 14, wherein the fixing element is a ring.

16. A method for removing a body-of-tissue (BOT) from a patient, the method comprising:
 i. excising the BOT thereby generating a cavity;
 ii. fixing one or more in-vivo-markers (IVMs) to walls of the cavity;
 iii. fixing one or more specimen markers (SpMs) to the BOT such that at least one location on the BTO that is associated with an SpM from the one or more SpMs is adjacent to a location in the cavity that is associated with an IVM from the one or more IVMs for generating at least one set of IVM and SpM's; and
 iv. wherein a unique electronic ID code is stored in a microelectronic chip that is associated with the at least one SpM from the one or more SpMs.

17. The method of claim 16, wherein the action of fixing an SpM from the one or more SpMs to the BOT is implemented by stitching the SpM to BOT.

18. The method of claim 16, wherein the action of fixing an SpM from the one or more SpMs to the BOT is implemented by using a clip.

19. The method of claim 16, further comprising recording the at least one set of IVM and SpM.

20. The method of claim 16, wherein at least one SpM from the one or more SpMs is associated with a unique feature that is configured to be visualized by an imaging system (VID).

21. The method of claim 20, wherein the imaging system comprises a mammography system.

22. The method of claim 16, wherein an SpM from the one or more SpMs comprises a fixing element.

23. The method of claim 22, wherein the fixing element is a ring.

* * * * *